United States Patent [19]

Liepmann et al.

[11] 4,338,314
[45] Jul. 6, 1982

[54] [1,2]ANELLATED-7-PHENYL-1,4-BEN-ZODIAZEPINE AND PHARMACEUTICAL COMPOSITIONS THEREOF AND USE FOR TREATMENT OF ULCERS

[75] Inventors: Hans Liepmann; Rolf Hueschens, both of Hanover; Wolfgang Milkowski, Burgdorf; Horst Zeugner; Insa Hell, both of Hanover; Klaus-Ullrich Wolf, Hänigsen, all of Fed. Rep. of Germany

[73] Assignee: Kali-Chemie Pharma GmbH, Hanover, Fed. Rep. of Germany

[21] Appl. No.: 67,146

[22] Filed: Aug. 16, 1979

[30] Foreign Application Priority Data

Aug. 16, 1978 [DE] Fed. Rep. of Germany ....... 2835708

[51] Int. Cl.$^3$ ................. C07D 487/04; C07D 489/04; C07D 513/04; A61K 31/55
[52] U.S. Cl. .................................... 424/246; 424/250; 424/248.4; 424/248.58; 260/239 R; 260/243.3
[58] Field of Search .................... 260/243.3; 424/246, 424/248.2, 250

[56] References Cited

U.S. PATENT DOCUMENTS

| | | | |
|---|---|---|---|
| 3,734,912 | 5/1973 | Hanze | 260/243.3 X |
| 3,822,259 | 7/1974 | Moffett | 260/243.3 R |
| 3,875,181 | 4/1975 | Derieg | 260/243.3 X |
| 3,900,490 | 8/1975 | Kuwada et al. | 260/239 BD |
| 3,941,799 | 3/1976 | Allgeier et al. | 260/239 BD |
| 4,006,135 | 2/1977 | Shenoy | 260/239 BD |

FOREIGN PATENT DOCUMENTS

| | | | |
|---|---|---|---|
| 327202 | 1/1976 | Austria . | |
| 1695211 | 5/1971 | Fed. Rep. of Germany . | |
| 2250425 | 5/1973 | Fed. Rep. of Germany . | |
| 2251291 | 5/1973 | Fed. Rep. of Germany . | |
| 2221558 | 11/1973 | Fed. Rep. of Germany . | |
| 2520937 | 11/1976 | Fed. Rep. of Germany . | |
| 7129150 | 10/1967 | Japan | 260/243 B |
| 573925 | 3/1976 | Switzerland . | |

Primary Examiner—David B. Springer
Attorney, Agent, or Firm—Schwartz, Jeffery, Schwaab, Mack, Blumenthal & Koch

[57] ABSTRACT

Compounds of [1,2]anellated-7-phenyl-1,4-benzodiazepines having the formula I

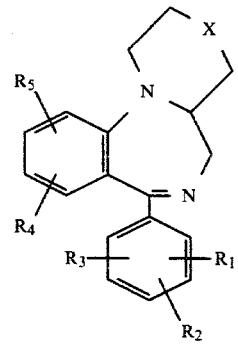

wherein
X is oxygen, sulfur or NR;
R is H,
$C_1$–$C_5$ alkyl,
$C_1$–$C_5$ alkyl, substituted with a terminal phenyl group, which is unsubstituted or substituted by one or 2 methoxy groups, a 3,4-methylene dioxy or 3,4-ethylenedioxy group,
$C_2$–$C_5$ alkyl, substituted with terminal halogen, hydroxy or methoxy or,
$C_3$–$C_5$ alkenyl
$R_1$, $R_2$, $R_3$, $R_4$ and $R_5$ are the same or different and are H, halogen, trifluoromethyl, nitro, alkyl, alkoxy, or alkylthio wherein alkyl is $C_1$–$C_4$ alkyl or two neighboring groups represent a methylenedioxy or ethylenedioxy group and the acid addition salts thereof, ulcer treating pharmaceutical compositions containing these compounds and a method of medical treatment using same.

22 Claims, No Drawings

[1,2]ANELLATED-7-PHENYL-1,4-BENZODIAZEPINE AND PHARMACEUTICAL COMPOSITIONS THEREOF AND USE FOR TREATMENT OF ULCERS

BACKGROUND OF THE INVENTION

The present invention relates to new [1,2]-anellated-7-phenyl-1,4-benzodiazepine derivatives, pharmaceutically acceptable salts thereof, processes for their preparation, pharmaceutical compositions thereof and methods of medical treatment using same.

It is known that 5-Phenyl-1,4-benzodiazepine derivatives such as, for example, 5-phenyl-1,4-benzodiazepine-2-one are pharmacologically effective in influencing the central nervous system and due to this central nervous activity also provides a certain stress ulcer inhibiting effect. This effect is not, however, sufficient to employ the substance for the pharmaceutical treatment of patients. It is known that the etiology of ulcer ailments is of a very complex nature. Because the pharmaceutical treatment previously employed only influenced partially the aspects of the many layered events associated with ulcers, only limited success could be achieved (see Blum, *Schweiz Med. Wochenschrift*, 106 (1976), p. 1475).

According to Demling (L. Demling, Klin. *Gastroenterologie I*, (1973), p. 202) the balance of active aggressive and defensive factors on the mucosa is disturbed in the case of stomach and intestinal ulcerations. A therapy must, therefore, directly be sufficient to restore the balance again.

It is known that psychopharmaceuticals, especially, 5-phenyl-1,4-benzodiazepine-2-one derivatives have a stress shielding effect and thereby present a certain stress ulcer inhibiting effect. These psychopharmaceuticals have not been successful in ulcer therapy, however, due to the limited effect with appropriate doses. Their central nervous system effects, e.g. sedative and the muscle tone influencing effects are undesirable in out patient therapies.

Ulcers of different pathologies over and above the ulcers influenced by stress are often unaffected by medication with psychopharmacologically active agents. Ulcers induced through pharmaceuticals such as the ulcers induced with indomethacine are exemplary.

SUMMARY OF THE INVENTION

It has surprisingly now been found that the novel [1,2]-anellated-7-phenyl-1,4-benzodiazepine derivatives possess only a comparatively low central nervous system activity, but instead, show a good ulcer inhibiting activity for ulcer afflictions arising from various origins such that it is equally applicable for ulcer therapy of the stomach as well as the duodenum.

The 1,2-anellated-1,4-benzodiazepine derivatives according to the present invention show a surprisingly good effect on ulcers of different pathologies over and above the ulcers influenced by stress.

In order to accomplish the objects and advantages according to the present invention, there are provided new compounds selected from the group of [1,2]-anellated-7-phenyl-1,4-benzodiazepines, having the formula I

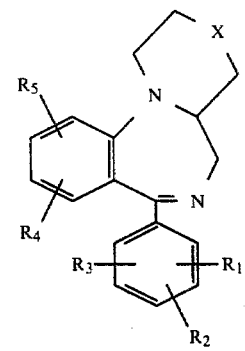

wherein
X is oxygen, sulfur or NR;
R is H,
$C_1-C_5$ alkyl,
$C_1-C_5$ alkyl, substituted with a terminal phenyl group which is unsubstituted or substituted with one or 2 methoxy groups, a 3,4-methylene dioxy or 3,4-ethylenedioxy group,
$C_2-C_5$-alkyl, substituted with terminal halogen, hydroxy or methoxy or,
$C_3-C_5$ alkenyl $R_1$, $R_2$, $R_3$, $R_4$ and $R_5$ are the same or different and are H, halogen, trifluoromethyl, nitro, alkyl, alkoxy or alkylthio wherein alkyl is $C_1-C_4$ alkyl or two neighboring groups represent a methylenedioxy or ethylenedioxy group and the acid addition salts thereof.

As alkyl or alkenyl groups on the nitrogen atom, several straight chain or branched chain groups having 1 to 5 carbon atoms are included. For example, methyl, ethyl, propyl, isopropyl, butyl, isobutyl, t-butyl, pentyl, isopentyl, neopentyl, allyl, 2 or 3-butenyl, 2,3 or 4 pentenyl groups. Preferred are the methyl and ethyl groups substituted with a terminal phenyl group, as well as ethyl and propyl groups with chloro, hydroxy or methoxy terminally substituted. Examples of halogen substituents $R_1$, $R_2$, $R_3$, $R_4$ and $R_5$ groups include, fluoro, chloro, bromo and iodo, especially, fluoro, chloro and bromo. The $C_1-C_4$ alkyl containing groups can be straight chain or branched chain alkyl, alkoxy or alkylthio-groups. In case of multiple substitution at the respective phenyl rings methyl containing groups such as, methyl, methoxy, methylthio or methylene dioxy are especially preferred.

With mono- or di-substitution on the phenyl ring of the 1,4-benzodiazepine group, the $R_4$ and $R_5$ components are preferably found in the 9 and/or 10 position. With the substituents being fluorine, nitro or trifluoromethyl groups, mono substitution in 9 position is preferred, for methoxy and methylthio, the 10 position is preferred.

At the 7-phenyl group, single substitution is preferably halogen, methyl, methoxy or trifluoromethyl in the 2' or 3' position. With multiple substitution on this group with either the same or different substituents, $R_1$, $R_2$ and $R_3$ substitution is preferred at the 3', 4'-or 3',4',5'-positions. Halogens, especially chlorine, and methyl, methoxy groups and/or methylenedioxy or ethylenedioxy groups are preferred as the substituents.

The new compounds and their salts provide valuable therapeutic qualities. They especially possess a pronounced ulcer inhibiting effect. At therapeutically effective doses the compounds of the subject invention or their acid addition salts do not show disturbing side effects such as sedation or influencing of the muscle tone. As a result of their low toxicity, the substances show a very good therapeutic ratio. The compounds are particularly useful for applications in out-patient ulcer treatment.

The compounds of Formula I

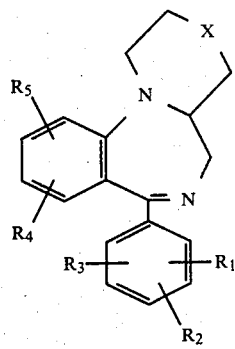

with X, $R_1$, $R_2$, $R_3$, $R_4$ and $R_5$ as defined above are prepared by cyclicizing at a temperature between about 60° and 120° C. in the presence of an inert solvent, the compound of Formula II

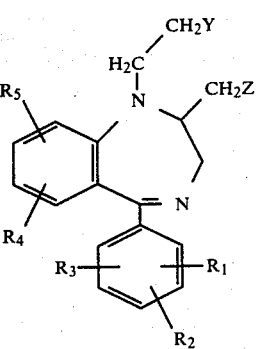

wherein $R_1$, $R_2$, $R_3$, $R_4$ and $R_5$ are defined as above and Y and Z represent the same or different reactive groups selected from the group consisting of halogen, especially chlorine or bromine, toluene, sulfonyloxy, benzene sulfonyloxy or methylsulfonyloxy in the presence of an alkali metal hydroxide or alkaline earth metal hydroxide, alkali metal carbonate or alkaline earth metal carbonate, alkali metal sulfate or alkaline earth metal sulfide or an amino compound $RNH_2$ whereby R is defined as above or the corresponding alkali metal amide. The base formed can be converted into an acid addition salt or the free base is isolated from the acid addition salt.

DESCRIPTION OF THE PREFERRED EMBODIMENTS

Preferred examples of the compounds of Formula II to be utilized as starting material are the compounds wherein Y and Z are identical. Especially advantageous is the introduction of the compound of Formula II in which Y and Z are chlorine. When the compounds of Formula II are employed wherein Y and Z are sulfonyl groups, the toluene sulfonyl group is proven to be especially useful. The compounds are prepared in a known manner from compounds of the Formula III

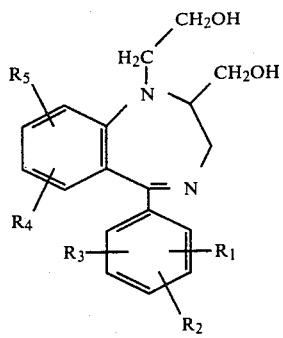

in which $R_1$, $R_2$, $R_3$, $R_4$ and $R_5$ are defined as above by way of a reaction with the corresponding sulfonyl chloride, for example, p-toluene sulfonyl chloride in the presence of an inert solvent. Under this procedure, it is not necessary to isolate the sulfonic acid ester formed thereby before conducting further reactions with compound II in the preparation of compound I.

In order to produce the anellated oxazino and thiazino[4,3-a][1,4]benzodiazepine derivatives I, the compounds of the general formula II are reacted, for example, with hydroxides, carbonates or sulfides of sodium, potassium, calcium or barium. In general, it is preferable to conduct the cyclization in the presence of an organic solvent, for example, alcohols, acetone, diethylether, dioxane, tetrahydrofurane, pyridine, dimethylsulfoxide or dimethylformamide whereby the addition of water can be advantageous. It is preferred to conduct the reaction with the components of the reaction in solution.

In the process of producing the anellated pyrazino-[1,2-a][1,4]-benzodiazepine, the same solvents can be employed, but it is also possible to utilize a primary organic amine as solvent.

The reaction of the process of the present invention can be carried out at normal pressure or at elevated pressures. During the cyclization step in the presence of ammonia or low-boiling amines, it is preferable to employ a closed vessel.

A subsequent substitution with a halogen or a nitro group in the phenyl ring of the 1,4-benzodiazepine system is also possible in a known manner. N-chlorosuccinamide or N-bromosuccinamide can serve as the halogenating agent for example. The conventional nitration reagents can be employed for the introduction of the nitro group, for example, copper (II) nitrate trihydrate in acetanhydride.

It is further possible to subsequently alkylate the NH group subsequently in the 1,2,3,4,4a,5-hexahydro-7-phenyl-pyrazino[1,2-a][1,4]benzodiazepine derivatives of Formula I in a known manner. The conventional methods are the reaction of these compounds with halogen alkyls (See Houben-Weyl, Volume XI/1 (1957) p. 24 et seq.), with dialkylsulfate, for example, dimethyl or diethyl sulfate or ethylene disulfate (page 207 of the above reference), with sulfonic acid esters of the formula R'-$SO_3R$, in which R', for example, is methyl, phenyl or 4-methylphenyl and R is an alkyl group (see the reference above at page 217), or with ethylene oxide and propylene oxide (page 311 of the above reference).

It is further possible to subsequently convert the hydroxy alkyl group of 1,2,3,4,4a,5-hexahydro-3-(hydroxy alkyl)-7-phenyl-pyrazino[1,2-a]benzodiazepines of Formula I into the methoxy alkyl group (see Houben-Weyl, positories, tablets, capsules, coated tablets and the like. The single doses for oral administration to adults range from 50 to 150 mg active compound and daily dose range from 150 to 450 mg.

The following non-limiting examples are intended to further illustrate the present invention.

EXAMPLE 1

A solution of 20 g 7-chloro-1-($\beta$-chloroethyl)2-chloromethyl-5-phenyl-2,3-dihydro-1H-1,4-benzodiazepine in 100 ml dioxane and 250 ml of 6% sodium hydroxide solution is heated under reflux for a period of about 5.5 hours. After heating the solution, the substance is isolated from chloroform under vacuum and subsequently purified chromatographically using aluminum oxide (activity degree II) as absorbent and methylene chloride as eluant. 12.8 g 1,2,4,4a-tetrahydro-9-chloro-7-phenyl-5H[1,4]oxazino-[4,3-a][1,4]benzodiazepine as an oil is obtained. The maleanate having a melting point of 143° to 145° C. is crystallized from isopropanol/ether. The basic compound crystallized from hexane melts at 156°–158° C.

In the similar manner from the following compounds: 1-($\beta$-chloroethyl)-2-chloromethyl-5-phenyl-2,3-dihydro-1H-1,4-benzodiazepine as well as the corresponding 7-fluoro-, 7-bromo-, 7-nitro-, 7-methyl-, 8-methyl-, 7-trifluoromethyl-, 7,8-dimethyl-, 8-methyloxy-, 7,8-dichloro-, 8-chloro-7-methyl-, 7-bromo-8-methyl-, 7,8-methylenedioxy- derivatives or the 7-chloro-1-($\beta$-chloroethyl)-2-chloromethyl-5-(3'-trifluoromethylphenyl)-2,3-dihydro-1H-1,4-benzodiazepine,7-chloro-1-($\beta$-chloroethyl)2-chloromethyl-5-(3',4'-dichlorophenyl)2,3-dihydro-1H-1,4-benzodiazepine or the 7-fluoro-1-($\beta$-chloroethyl)-2-chloromethyl-5-(3',4',5'-trimethoxyphenyl)-2,3-dihydro-1H-1,4-benzodiazepine are obtained the following compounds:

| | Melting Point °C. |
|---|---|
| 1,2,4,4a-tetrahydro-7-phenyl-5H[1,4]oxazino-[4,3-a][1,4]benzodiazepine | 102–105 |
| 1,2,4,4a-tetrahydro-9-fluoro-7-phenyl-5H-[1,4]oxazino[4,3-a][1,4]benzodiazepine | 154–156 |
| 1,2,4,4a-tetrahydro-9-bromo-7-phenyl-5H-[1,4]oxazino[4,3-a][1,4]benzodiazepine | 176–179 |
| 1,2,4,4a-tetrahydro-9-nitro-7-phenyl-5H-[1,4]oxazino[4,3-a][1,4]benzodiaepine | 142–145 |
| 1,2,4,4a-tetrahydro-9-methyl-7-phenyl-5H-[1,4]oxazino[4,3-a][1,4]benzodiazepine | 174–176 |
| 1,2,4,4a-tetrahydro-10-methyl-7-phenyl-5H-[1,4]oxazino[4,3-a][1,4]benzodiazepine | 123–124 |
| 1,2,4,4a-tetrahydro-9-trifluormethyl-7-phenyl-5H-[1,4]oxazino[4,3-a][1,4]benzodiazepine | oil* |
| 1,2,4,4a-tetrahydro-9,10-dimethyl-7-phenyl-5H[1,4]oxazino[4,3-a][1,4]benzodiazepine | 132–134 |
| 1,2,4,4a-tetrahydro-10-methoxy-7-phenyl-5H-[1,4]oxazino[4,3-a][1,4]benzodiazepine | 107–110 |
| 1,2,4,4a-tetrahydro-9,10-dichloro-7-phenyl-5H[1,4]oxazino[4,3-a][1,4]benzodiazepine | 163–165 |
| 1,2,4,4a-tetrahydro-10-chloro-9-methyl-7-phenyl-5H[1,4]oxazino[4,3-a][1,4]benzodiazepine | 115–118 |
| 1,2,4,4a-tetrahydro-9-bromo-10-methyl-7-phenyl-5H[1,4]oxazino[4,3-a][1,4]benzodiazepine | 117–119 |
| 1,2,4,4a-tetrahydro-9,10-methylenedioxy-7-phenyl-5H[1,4]oxazino[4,3-a][1,4]benzodiazepine | 156–158 |
| 1,2,4,4a-tetrahydro-9-chloro-7-(3'-trifluoromethylphenyl-5H[1,4]oxazino[4,3-a][1,4]benzodiazepine | 104–107 |
| 1,2,4,4a-tetrahydro-9-chloro-7-(3',4'-dichlorphenyl-5H[1,4]oxazino[4,3-a][1,4]-benzodiazepine | 145–148 |
| 1,2,4,4a-tetrahydro-9-fluoro-7-(3',4',5'-trimethoxyphenyl)-5H[1,4]oxazino-[4,3-a][1,4]-benzodiazepine | 165–166 |

*IR-spectrum(oil): 1615 cm$^{-1}$ (C=N)

EXAMPLE 2

To a stable suspension of 8.0 g 7-chloro-1-($\beta$-hydroxyethyl)-2-hydroxymethyl-5-(2'-chlorophenyl)2,3-dihydro-1H-1,4-benzodiazepine and 5.2 g p-toluenesulfochloride in 80 ml dioxan is added a solution of 5.2 g potassium hydroxide in 17.2 ml of water and subsequently the mixture is heated under reflux for one hour. The organic phase is separated from the water phase and removed under vacuum. The reaction products are isolated from chloroform. After chromatographic purification using aluminum oxide (activity degree II) with chloroform, 4.8 g of 1,2,4,4a-tetrahydro-9-chloro-7-(2'-chlorophenyl)-5H[1,4]oxazino[4,3-a][1,4]benzodiazepine having a melting point of 140°–141° C. are obtained.

Similarly, 1,2,4,4a-tetrahydro-7-(2'-chlorphenyl)-5H[1,4]oxazino[4,3-a][1,4]benzodiazepine as oil, (IR: 1615 cm$^{-1}$ (C=N)) 1,2,4,4a-tetrahydro-7-(2'fluorphenyl)-5H-[1,4]oxazino[4,3a][1,4]benzodiazepine as oil (IR: 1610 cm$^{-1}$ (C=N)) can be obtained from 1-($\beta$-hydroxyethyl)-2-hydroxymethyl-5-(2'-chlorophenyl)-2,3-dihydro-1H-1,4-benzodiazepine and 1-($\beta$-hydroxyethyl)-2-hydroxymethyl-5-(2'-fluorophenyl)2,3-dihydro-1H-1,4-benzodiazepine, respectively.

EXAMPLE 3

10 g of 7-chloro-1-($\beta$-chlorethyl)-2-chlormethyl-5-phenyl-2,3-dihydro-1H-1,4-benzodiazepine are heated under reflux in 100 ml of ethanol with 7.2 g of sodium sulfide mona-hydrate for four hours. The solvent is separated under vacuum and the reaction product is isolated from chloroform. After chromatographical purification from aluminum oxide (activity level II) with methylene chloride and crystallization from hexane 5.4 g of 1,2,4,4a-tetrahydro-9-chloro-7-phenyl-5H[1,4]thiazino[4,3-a][1,4]benzodiazepine having a melting point of 136° to 138° C. are obtained.

In a similar manner from 1-($\beta$-chlorethyl)2-chlormethyl-5-phenyl-2,3-dihydro-1H-1,4-benzodiazepine, and its 7-fluoro-, 7-nitro-, 7-methyl- and 8-methoxy derivatives as well as its 2'fluorphenyl derivatives and similarly 7-chloro-1-($\beta$-chlorethyl)-2-chlormethyl-5-(3'-trifluormethylphenyl)-2,3-dihydro-1H-1,4-benzodiazepine the following compounds can be obtained:

| | Melting Point °C. |
|---|---|
| 1,2,4,4a-tetrahydro-7-phenyl-5H[1,4]thiazino-[4,3-a][1,4]benzodiazepine | 125–128 |
| 1,2,4,4a-tetrahydro-9-fluoro-7-phenyl-5H-[1,4]thiazino[4,3-a][1,4]benzodiazepine | 168–170 |
| 1,2,4,4a-tetrahydro-9-nitro-7-phenyl-5H-[1,4]thiazino[4,3-a][1,4]benzodiazepine | 166–172 |
| 1,2,4,4a-tetrahydro-9-methyl-7-phenyl-5H-[1,4]thiazino[4,3-a][1,4]benzodiazepine | 143–146 |
| 1,2,4,4a-tetrahydro-10-methoxy-7-phenyl-5H-[1,4]thiazino[4,3-a][1,4]benzodiazepine | 125–131 |
| 1,2,4,4a-tetrahydro-7-(2'-fluorphenyl)-5H[1,4]thiazino[4,3-a][1,4]benzodiazepine IR: 1610 cm$^{-1}$ (C = N) | oil |
| 1,2,4,4a-tetrahydro-9-chloro-7-(3'-trifluormethylene)-5H[1,4]- | |

Volume VI/3 (1965) page 24) or into the halogen alkyl group (page 862 of the same reference Volume V/3 (1962).

The production of the 1,4-benzodiazepine derivatives of Formula II wherein $R_1, R_2, R_3, R_4$ and $R_5$ have the same meaning as indicated above and Y and Z are halogen atoms, as well as of the 1,4-benzodiazepine derivatives of Formula III wherein $R_1$, $R_2$, $R_3$, $R_4$, and $R_5$ are defined as above are described in German Offenlegunsschrift No. 22 21 558 as well as in German Patent Specification No. 25 20 937 both of which are incorporated herein by reference.

As the principal reaction, the cyclization of acyl diamines with phosphoroxy chlorides at a temperature between about 90° and 130° C. is employed. Thereby the 1,4-benzodiazepine derivative of Formula II are obtained directly or a mixture of 1,5-benzodiazocines and 1,4-benzodiazepines is obtained which subsequently can be converted into the 1,4-benzodiazepine derivatives by means of treatment with nucleophylic reagents.

DESCRIPTION OF THE PHARMACOLOGICAL TEST METHODS

1. Acute Toxicity:

The acute 7-day toxicity is determined after a single application per os in white NMRI mice which have not been fed. The calculation of the $LD_{50}$ is carried out by probitananalysis by means of electronic data processing (see L. Cavalli-Sforza, Gustav-Fischer-Verlag, Stuttgart (1964), Grundbegriffe der Biometrie, Chapter 10, pages 153–190).

2. Effectiveness Against Indomethacine-Induced Ulcers in Rats Modified Test Procedure According to U. Jahn and R. W. Adrian, Arzneimittel Forschung, (Drug Research) 19, (1969), p. 36.:

To at least six male rats having a body weight of from 155 to 190 g dosages of the test compounds are administered orally in an amount of 0.5 ml of a suspension medium per 100 g animal weight. The animals of the blank control group receive the corresponding amount by volume of the suspension medium only. One hour after the application of the test compouns, a dosage of 40 mg/kg of indomethacine contained in an amount of 0.5 ml of a suspension per 100 g animal weight are orally applied to each animal for producing ulcers. Twenty-four hours after the application of the indomethacine the animals are sacrificed.

The evaluation is carried out by a modification of the method of O. Muenchow, (Arznein. Forsch. (Drug Res.) 4, (1954) page 341 and 344. The mean value and standard deviation of the numbers of ulcers is calculated and subsequently the inhibiting activity of the test compounds and a standard compound are calculated as percent inhibition compared with the blank control group.

3. Testing of Musculatropic Properties:

In a traction test, mice are administered the test substance orally. After 120 minutes the mice are attached at the front paws to a horizontally suspended wire. The $ED_{50}$ is the dose which causes exactly half of the animals not to touch the wire also with their hind legs within a period of 5 seconds, (W. Theobald et al, Arneim. Forschung 17, (1967), page 561). This test measures the influence of the test substance on the muscle tone of the test subject.

4. Testing of Central Nervous Depressant Properties (Prolonging the Hexobarbital sleep time):

The test substance is administered orally to mice. After 30 minutes, the animals are additionally injected with hexabarbitol in an amount of 64 mg/kg. The time point of the onset of sleeping posture is determined and the duration of sleeping posture is compared with a control group treated exclusively with hexobarbitol. The dose, with which half of the animals extend the time of sleeping posture by a factor of 4 over that of the control group, is defined as $ED_{50}$. (J. W. Kemp. M. Tannhauser and E. A. Swingard, Arch. Int. Pharmacodyn. 193(1971), pp 34–47).

The following compounds were tested according to the foregoing tests:

(a) 1,2,4,4a-tetrahydro-9-chloro-7-phenyl-5H[1,4]oxazino-[4,3-a][1,4]benzodiazepin-maleinate (b) 1,2,4,4a-tetrahydro-9-fluoro-7-phenyl-5H[1,4]oxazino-[4,3-a][1,4]benzodiazepine (c) 1,2,4,4a-tetrahydro-9-methyl-7-phenyl-5H[1,4]oxazino[4,3-a][1,4]benzodiazepine (d) 1,2,4,4a-tetrahydro-10-methyl-7-phenyl-5H[1,4]oxazino-[4,3-a][1,4]benzodiazepine (e) 1,2,4,4a-tetrahydro-9-chloro-5-(2'chlorphenyl)5H[1,4]oxazino[4,3a][1,4]benzodiazepine (f) 1,2,4,4a-tetrahydro-10-methoxy-7-phenyl-5H[1,4]oxazino[4,3-a][1,4]benzodiazepine (g) 1,2,4,4a-tetrahydro-10-chloro-9-methyl-7-phenyl-5H[1,4]oxazino[4,3-a][1,4]benzodiazepine (h) 1,2,4,4a-tetrahydro-9-chloro-7-phenyl-5H[1,4]thiazino[4,3-a][1,4]benzodiazepine (i) 1,2,3,4,4a,5-hexahydro-9-chloro-3-allyl-7-phenyl-pyrazino[1,2-a][1,4]benzodiazepin-dihydrochloride.1.5 Mol $H_2O$.0.3 mole Isopriopanol (k) 1,2,3,4,4a,5-hexahydro-9-chloro-3-phenethyl-7-phenyl-pyrazino[1,2-a][1,4]benzodiazepine (l) 1,2,3,4,4a,5-hexahydro-3,9-dimethyl-7-phenyl-pyrazino[1,2-a][1,4]benzodiazepin-dihydrochloride.1.5 mole $H_2O$ (s) Standard: 7-chloro-1-methyl-5-phenyl-1,3-dihydro-2H-1,4-benzodiazepin-2-one (Diazepam)

TABLE

| Substance | $LD_{50}$ p.o. (mg/kg) | Ulcer Induced by Indomethacine | | Traction test $ED_{50}$ (mg/kg) | Prolonging Hexobarbitol Sleep Time (mg/kg) |
| --- | --- | --- | --- | --- | --- |
| | | (mg/kg) | % Inhibited | | |
| A | 2260 | 150 | 61 | 285.0 | 31.6 |
| B | >1370 | 100 | 77 | >296 | 80.3 |
| C | >1430 | 200 | 68 | >316 | 139 |
| D | >1470 | 100 | 70 | >316 | 138 |
| E | >1470 | 100 | 86 | >316 | 11.8 |
| F | >1430 | 100 | 42 | >308 | 202 |
| G | >1520 | 200 | 77 | >327 | 119 |
| H | >1470 | 100 | 74 | 316 | 153 |
| I | 1090 | 200 | 81 | >316 | 100 |
| K | >1310 | 200 | 85 | >284 | 110 |
| L | >1010 | 250 | 70 | >215 | 164 |
| S | 887 | 12* | 28 | 4.2 | 1.5 |

*The standard, Diazepam, shows already with small doses a strong psychopharmacological effect, such that higher doses sufficient to achieve an improved ulcer inhibiting effect are not tolerable.

From the results obtained, it is demonstrated that the compounds of the present invention display good ulcer treating effects with minimal central nervous system effects.

The compounds of Formula I and their salts lend themselves to be worked up in the known manner by addition to physiologically acceptable carriers and additives or supplemental agents into suitable pharmaceutical dosage forms, such as for example, solutions, sup-

| | Melting Point °C. |
|---|---|
| thiazino[4,3-a][1,4]benzodiazepine | 102–104 |

EXAMPLE 4

10 g 7-chloro-1-(β-chlorethyl)-2-chlormethyl-5-phenyl-2,3-dihydro-1H-1,4-benzodiazepine were reacted in 200 ml methanol with 20 g ammonia gas in a gas autoclave for 16 hours at 90° to 95° C. After heating of the solution under vacuum, the reaction material is yielded in chloroform and washed with dilute aqueous sodium hydroxide solution. After drying and evaporating of the solvent under vacuum the resultive oily reaction product is dissolved in ether. From the concentrated solution, 5 g of 1,2,3,4,4a,5-hexahydro-9-chloro-7-phenyl-pyrazino[1,2-a]-[1,4]benzodiazepine having a melting point of 132°–135° C. are obtained by crystallization.

In a similar manner, from 1-(β-chlorethyl)-2-chlormethyl-5-phenyl-2,3-dihydro-1H-1,4-benzodiazepine, and its 7-bromo-, 7-methyl-, 8-methoxy-, 7,8-dimethyl- and 7-bromo-8-methyl derivatives, 7-chloro-1-(β-chlorethyl)-2-chlormethyl-5-(2'chlorphenyl)-2,3-dihydro-1H-1,4-benzodiazepine, 7-chloro-(β-chlorethyl)-2,chlormethyl-5-(3',4'-dichlorphenyl)-2,3-dihydro-1H-1,4-benzodiazepine and 7-bromo-1-(β-chlorethyl)-2-chlormethyl-5-(3',4'-dichlorphenyl)-2,3-dihydro-1H-1,4-benzodiazepine the following compounds can be obtained.

| | Melting Point °C. |
|---|---|
| 1,2,4,4a,5-hexahydro-7-phenyl-pyrazino[1,2-a][1,4]benzodiazepine IR: 3500 cm$^{-1}$ (NH) 1610 cm$^{-1}$ (C = N) | Oil |
| 1,2,3,4,4a-hexahydro-9-bromo-7-phenyl-pyrazino[1,2-a][1,4]benzodiazepine | 133–138 |
| 1,2,3,4,4a,5-hexahydro-9-methyl-7-phenylpyrazino[1,2-a][1,4]benzodiazepine (ditpsylate) | 192–198 |
| 1,2,3,4,4a,5-hexahydro-10-methoxy-7-phenyl-pyrazino[1,2-a][1,4]benzodiazepine IR: 3500 cm$^{-1}$ (NH) 1610 cm$^{-1}$ (C = N) | Oil |
| 1,2,3,4,4a,5-hexahydro-9,10-dimethyl-7-phenylpyrazino[1,2-a]-[1,4]benzodiazepine(ditosylate) | 232–234 |
| 1,2,3,4,4a,5-hexahydro-9-bromo-10-methyl-7-phenyl-pyrazino[1,2-a]-[1,4]benzodiazepine(ditosylate) | 260–263 |
| 1,2,3,4,4a,5-hexahydro-9-chloro-7-(2'-chlorphenyl)-pyrazino[1,2-a]-[1,4]benzodiazepine | 131–137 |
| 1,2,3,4,4a,5-hexahydro-9-chloro-7-(3',4'-dichlorphenyl)-pyrazino-[1,2-a][1,4]benzodiazepine IR: 3500 cm$^{-1}$ (NH) 1610 cm$^{-1}$ (CN) | Oil |
| 1,2,3,4,4a,5-hexahydro-9-bromo-7-(3',4'-dichlorophenyl)-pyrazino-[1,2-a][1,4]benzodiazepindihydrochloride . 1 Mol isopropanol 0.3 H$_2$O | 210–212 |

EXAMPLE 5

18.4 g 7-chloro-1-(β-chlorethyl)-2-chlormethyl-5-phenyl-2,3-dihydro-1H-1,4-benzodiazepine are reacted in 200 ml of methanol with 10 g methylamine for 16 hours at about 110° C. in a glass autoclave. After working up the reaction product, there are obtained 12 g 1,2,3,4,4a,5-hexahydro-9-chloro-3-methyl-7-phenyl-pyrazino[1,2-a][1,4]benzodiacepindihydrochloride.1 mole H$_2$O having a melting point of 262° C. (under decomposition). In a similar manner, the following compounds can be obtained from 7-chloro-1-(β-chlorethyl)-2-chlormethyl-5-phenyl-2,3-dihydro-1H-1,4-benzodiazepine upon reaction in methanol with (a) isopropylamine, (b) n-butylamine, (c) t-butylamine, (d) allylamine, (e) ethanolamine and (f) β-(3,4-dimethoxyphenyl)-ethylamine:

| | Melting Point °C. |
|---|---|
| (a) 1,2,3,4,4a,5-hexahydro-9-chloro-3-isopropyl-7-phenyl-pyrazino[1,2-a]-[1,4]benzodiazepindihydrochloride . 2.5 mole H$_2$O | 236–245* |
| (b) 1,2,3,4,4a,5-hexahydro-9-chloro-3-butyl-7-phenyl-pyrazino[1,2-a]-[1,4]benzodiazepine | 104–106 |
| (c) 1,2,3,4,4a,5-hexahydro-9-chloro-3-tert.-butyl-7-phenyl-pyrazino[1,2-a][1,4]benzodiazepine | 143–146 |
| (d) 1,2,3,4,4a,5-hexahydro-9-chloro-3-allyl-7-phenyl-pyrazino[1,2-a][1,4]benzodiazepine-dihydrochloride . 1.5 moles H$_2$O . 0.3 Mol isopropanol | 230–233* |
| (e) 1,2,3,4,4a,5-hexahydro-9-chloro-3-(β-hydroxyethyl)-7-phenyl-pyrazino[1,2][1,4]benzodiazepine as dihydrochloride . 2.5 mole H$_2$O | 129–131 216* |
| (f) 1,2,3,4,4a,5-hexahydro-9-chloro-3-(3,4-dimethoxyphenethyl)-7-phenyl-pyrazino[1,2-a][1,4]benzodiazepine-dihydrochloride-dihydrate | 180* |

*under decomposition.

EXAMPLE 6

Reacting methylamine in a methanol solution at a temperature between 90°–95° C. in a glass autoclave with the following:

(a) 7-chloro-1-(β-chlorethyl)-2-chlormethyl-5-(2'-chlorphenyl)-2,3-dihydro-1H-1,4-benzodiazepine (b) 7-chloro-1-(β-chlorethyl)-2-chlormethyl-5-(2'-methoxyphenyl)-2,3-dihydro-1H-1,4-benzodiazepine (c) 7-methyl-1-(β-chlorethyl)-2-chlormethyl-5-phenyl-2,3-dihydro-1H-1,4-benzodiazepine (d) 8-methyl-1-(β-chlorethyl)-2-chlormethyl-5-phenyl-2,3-dihydro-1H-1,4-benzodiazepine (e) 8-methyl-1-(β-chlorethyl)-2-chlormethyl-5-(2'-chlorphenyl)-2,3-dihydro-1H-1,4-benzodiazepine (f) 7-bromo-8-methyl-1-(β-chlorethyl-2-chlormethyl-5-(2'-chlorphenyl)-2,3-dihydro-1H-1,4-benzodiazepine (g) 7,8-dimethyl-1-(β-chlorethyl)-2-chlormethyl-5-phenyl-2,3-dihydro-1H-1,4-benzodiazepine (h)–(m) 1-(β-chlorethyl)-2-chlormethyl-5-phenyl-2,3-dihydro-1H-1,4-benzodiazepin and their 7-fluoro-, 7-nitro-, 7,8-dichloro- and 8-methoxy derivatives (n) 1-(β-chlorethyl)-2-chlormethyl-5-(2'-chlorphenyl)-2,3-dihydro-1,4-benzodiazepine the following compounds are obtained:

| | Melting Point °C. |
|---|---|
| (a) 1,2,3,4,4a,5-hexahydro-9-chloro-3-methyl-7-(2'-chlorphenyl)-pyrazino-[1,2-a][1,4]-benzodiazepine | 137–138 |
| (b) 1,2,3,4,4a,5-hexahydro-9-chloro-3-methyl-7-(2'-methoxyphenyl)-pyrazino-[1,2-a][1,4]-benzodiazepine IR: 1615 cm$^{-1}$ (C = N) | Oil |
| (c) 1,2,3,4,4a,5-hexahydro-3,9-dimethyl-7-phenyl-pyrazino[1,2-a][1,4]benzodiazepine- | |

-continued

| | Melting Point °C. |
|---|---|
| dihydrochloride . 1.5 Mol H₂O | 230–233 |
| (d) 1,2,3,4,4a,5-hexahydro-3,10-dimethyl-7-phenyl-pyrazino[1,2-a]-[1,4]benzodiazepine | 164–165 |
| (e) 1,2,3,4,4a,5-hexahydro-3,10-dimethyl-7-(2'-chlorphenyl)-pyrazino-[1,2-a][1,4]-benzodiazepine | 145–147 |
| (f) 1,2,3,4,4a,5-hexahydro-9-bromo-3,10-dimethyl-7-(2'-chlorphenyl)-pyrazino[1,2-a][1,4]benzodiazepine | 106–108 |
| (g) 1,2,3,4,4a,5-hexahydro-3,9,10-trimethyl-7-phenyl-pyrazino[1,2-a][1,4]-benzodiazepine | 139–140 |
| (h) 1,2,3,4,4a,5-hexahydro-3-methyl-7-phenylpyrazino[1,2-a][1,4]benzodiazepin | 111–114 |
| (i) 1,2,3,4,4a,5-hexahydro-9-fluoro-3-methyl-7-phenyl-pyrazino[1,2-a][1,4]-benzodiazepindihydrochloride . 0.3 mole ethanol | 200* |
| (k) 1,2,3,4,4a,5-hexahydro-9-nitro-3-methyl-7-phenyl-pyrazino[1,2-a][1,4]-benzodiazepine | 191–194 |
| (l) 1,2,3,4,4a,5-hexahydro-9,10-dichloro-3-methyl-7-phenyl-pyrazino-[1,2-a][1,4]benzodiazepine | 158–160 |
| (m) 1,2,3,4,4a,5-hexahydro-10-methoxy-3-methyl-7-phenyl-pyrazino-[1,2-a][1,4]benzodiazepine | 121–123 |
| (n) 1,2,3,4,4a,5-hexahydro-3-methyl-7-(2'-chlorphenyl)-pyrazino[1,2-a]-[1,4]benzodiazepine | 136–138 |

*decomposing

EXAMPLE 7

3.7 g 7-chloro-1-(β-chlorethyl)-2-chlormethyl-5-phenyl-2,3-dihydro-1H-1,4-benzodiazepine are heated in 50 ml benzylamine for about 5.5 hours at 120° C. Subsequently, unreacted benzylamine is removed under vacuum and the reaction product is mixed with dilute sodium hydroxide solution and isolated from chloroform. From ethanol 1,2,3,4,4a,5-hexahydro-9-chloro-3-benzyl-7-phenyl-pyrazino[1,2-a][1,4]benzodiazepinedihydrochloride.1 mole H₂O.1 mole ethanol is crystallized out having a melting point of 236°–239° C. (decomposition). Yield 3 g.

From reaction of 7-chloro-1-(β-chlorethyl)2-chlormethyl-5-phenyl-2,3-dihydro-1H-1,4-benzodiazepine with the following compounds β-methoxyethylamine, 1,3-aminopropanol, phenethylamine, isopentylamine and neopentylamine the following reaction products are obtained:

| | Melting Point °C. |
|---|---|
| (a) 1,2,3,4,4a,5-hexahydro-9-chloro-3-(β-methoxyethyl)-7-phenylpyrazino-[1,2-a][1,4]benzodiazepindihydrochloride . 0.7 mole H₂O | 237–240 |
| (b) 1,2,3,4,4a,5-hexahydro-9-chloro-3-(γ-hydroxypropyl)-7-phenylpyrazino-[1,2-a][1,4]benzodiazepindihydrochloride . 1 mole H₂O | 205* |
| (c) 1,2,3,4,4a,5-hexahydro-9-chloro-3-(phenyethyl)-7-phenylpyrazino-[1,2-a][1,4]benzodiazepine | 119–121 |
| (d) 1,2,3,4,4a,5-hexahydro-9-chloro-3-isopentyl-7-phenylpyrazino[1,2-a]-[1,4]benzodiazepindihydrochloride . 0.5 mole H₂O . 1 Mol ethanol | 240–245 |
| (e) 1,2,3,4,4a,5-hexahydro-9-chloro-3-neopentyl-7-phenylpyrazino[1,2-a]-[1,4]benzodiazepindihydrochloride . 0.3 mole H₂O . 1 Mol ethanol | 215* |

*decomposing

EXAMPLE 8

4 g 1,2,3,4,4a,5-hexahydro-9-chloro-3-(β-hydroxyethyl)-7-phenyl-pyrazino[1,2-a][1,4]benzodiazepindihydrochloride.2.5 mole H₂O are heated under reflux with 15 ml thionylchloride for 20 minutes. The solvent is subsequently removed and the base yielded with dilute water sodium hydroxide solution under cooling with ice and subsequently isolated from chloroform. 3.2 g of 1,2,3,4,4a,5-hexahydro-9-chloro-3-(β-chlorethyl)7-phenyl-pyrazino[1,2-a][1,4]benzodiazepinedihydrochloride.1.0 mole H₂O.0.6 mole Isopropanol has been crystallized from isopropanol said compound having a freezing point of 220° C. (decomposing).

EXAMPLE 9

5.5 g 1,2,4,4a-tetrahydro-7-(2'-chlorphenyl)-5H-[1,4]oxazino[4,3]-a[1,4]benzodiazepine are dissolved in 45 ml acetic anhydride and at 35° C. 5.4 g copper (II) nitrate trihydrate are added gradually, the temperature is held at about 1.5 hours and the reaction solvent subsequently is cooled with ice. After treatment with dilute sodium hydroxide solution and ammonia solution, the reaction product is isolated from chloroform. After chromatographic purification with aluminum oxide (activity step II) as absorbent and methylene chloride/-chloroform 2 g 1,2,4,4a-tetrahydro-9-nitro-7-(2'chlorphenyl)-5H[1,4]oxazino[4,3-a]-benzodiazepine crystallizes from ether. The compound has a melting point of 164°–166° C. Also produced are 1.2 g of the isomer 1,2,4,4a-tetrahydro-11-nitro-7-(2'chlorphenyl)-5H[1,4]oxazino[4,3-a][1,4]benzodiazepine as an oil. (IR spectrum 1595, 1615 cm⁻¹ (C═C, C═N).

Correspondingly, from the 5-phenyl substituted derivative, the following compounds are obtained: 1,2,4,4a-tetrahydro-9-nitro-7-phenyl-5H[1,4]oxazino[4,3-a][1,4]benzodiazepine with a melting point of 142°–145° C. and 1,2,4,4a-tetrahydro-11-nitro-7-phenyl-5H[1,4]oxazino-[4,3-a][1,4]benzodiazepine with a melting point of 184°–186° C.

EXAMPLE 10

4.9 g 1,2,3,4,4a-5-hexahydro-9-chloro-3-(β-chlorethyl-7-phenyl-pyrazino[1,2-a][1,4]benzodiazepinedihydrochloride.1.0 mole H₂O.0.6 mole isopropanol are added to a solution of 0.75 g sodium in 70 ml of methanol and heated for 5 hours under reflux. After distilling off the solvent, the remaining residue is dissolved in chloroform and the organic phase is washed with water. After distilling off the solvent 3.3 g 1,2,3,4,4a,5-hexahydro-9-chloro-3-(β-methoxyethyl)-7-phenyl-pyrazino[1,2-a][1,4]-benzodiazepine are obtained. The substance crystallizes as a dihydrochloride with 0.7 mole of water from ethanol and has a melting point of 237°–240° C.

EXAMPLE 11

4 g 1,2,3,4,4a,5-hexahydro-9-chloro-3-(β-hydroxyethyl)-7-phenyl-pyrazino[1,2-a][1,4]benzodiazepinedihydrochloride.2.5 mole H₂O is added to 0.8 g sodium hydride in 100 ml of diethylformamide. After addition of 1.5 g of methyl halide the reaction solution is maintained for 4 hours at ambient temperature. The raw product obtained upon distilling off the solvent is purified chromatagraphically with aluminum oxide (activity step II) with chloroform. 1.7 g 1,2,3,4,4a,5-hexahydro-9-chloro-3-(β-methoxyethyl)-7-phenyl-pyrazino[1,2-a][1,4]benzodiazepine are obtained. The substance crystallizes as a dihydrochloride with 0.7 mole of water from ethanol and has a melting point of 237°–240° C.

EXAMPLE 12

10 g 1,2,4,4a-tetrahydro-5-(2'-fluorphenyl)-5H[1,4]oxazino[4,4-a][1,4]benzodiazepine are heated in 150 ml methylene chloride with 6 g in bromosuccinimide for 3.5 hours under reflux. After the customary procedures are carried out 4.0 g oily 1,2,4,4a-tetrahydro-9-bromo-7-(2'fluorphenyl)-5H[1,4]oxazino[4,3-a][1,4]-benzodiazepine are produced (Infrared spectrum 1610 cm$^{-1}$.

EXAMPLE 13

Capsules are prepared containing 100 mg 1,2,4,4a-tetrahydro-9-chloro-7-phenyl-5H-[1,4]thiazino-[4,3-a][1,4]benzodiazepine as active agent. The complete capsule ingredients include:

| Pharmacologically Active Agent | 100 mg |
|---|---|
| Lactose | 90 mg |
| Aerosil 200 (Commercial Product highly dispersed silicic acid, manufacturer Degussa) | 4 mg |
| Talc | 4 mg |
| Magnesium stearate | 2 mg |
| | 200 mg |

Production method:
the pharmacologically active agent is mixed with the additional ingredients and filled into size 2 capsules. The other pharmcologically active agents also can be manufactured into capsules containing 100 ml pharmacologically active agent together with the named additional ingredients in this manner.

EXAMPLE 14

Tablets are prepared containing 50 ml 1,2,4,4a-tetrahydro-9-chloro-7-phenyl-5H[1,4]oxazino[4,3-a][1,4]benzodiazepine-maleinate, each tablet containing:

| Pharmacologically Active Agent | 50 mg |
|---|---|
| Lactose | 60 mg |
| Cornstarch | 30 mg |
| Primogel (Commercial product carboxymethylcellulose, manufacturer Scholtens Chemische Fabrichen N.V.) | 4 mg |
| Gelatin | 2 mg |
| Aerosil 200 (Commercial product highly dispersed silicic acid, manufacturer Degussa) | 2 mg |
| Magnesium stearate | 2 mg |
| | 150 mg |

Tablets are produced according to the following method. The gelatin and water are made into a 10 percent mucilage. The active ingredient lactose, cornstarch and primogel are mixed. The mixture and mucilage then are granulated together through a sieve of 1.5 ml mesh size. The granulate is dried at 40° C., once more passed through the sieve, mixed with the highly dispersed silicic acid (Aerosil 200) and the magnesium stearate and the mixture pressed into tablets using a die having a diameter of 9 mm.

EXAMPLE 15

A coated tablet containing 50 ml 1,2,3,4,4a,5-hexahydro-3,9-dimethyl-7-phenyl-pyrazino[1,2-a][1,4]benzodiazepine-dihydrochloride.1.5 mole H$_2$O as a pharmacologically active ingredient are prepared.

According to the procedure described in Example 14, tablets containing the pharmacologically active ingredient are prepared and subsequently coated in a conventional manner. The resulting coated tablets are polished with the aid of beeswax.

What is claimed is:
1. A compound selected from the group of [1,2]anellated-7-phenyl-1,4-benzodiazepines having the Formula I

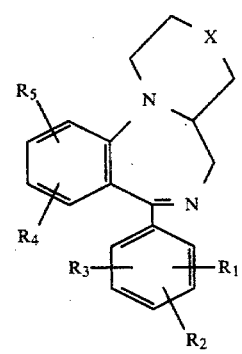

wherein
X is oxygen, sulfur or NR;
R is H,
C$_1$–C$_5$ alkyl,
C$_1$–C$_5$ alkyl, substituted with a terminal phenyl group, or a terminal phenyl group substituted with one or 2 methoxy groups, 3,4-methylenedioxy group or 3,4-ethylenedioxy group,
C$_2$–C$_5$ alkyl, substituted with terminal halogen, hydroxy or methoxy or,
C$_3$–C$_5$ alkenyl
R$_1$, R$_2$, R$_3$, R$_4$ and R$_5$ are the same or different and are H, halogen, trifluoromethyl, non-sterically hindering nitro, alkyl, or alkoxy wherein alkyl is non-sterically hindering C$_1$–C$_4$ alkyl or two neighboring groups together represent methylenedioxy or ethylenedioxy group and the pharmaceutically acceptable acid addition salts thereof.
2. The compound of claim 1 wherein R$_4$ and R$_5$ are in the 9 and 10 position of the 1,4-benzodiazepine and are selected from the group consisting of H, Cl, Br and CH$_3$.
3. The compound of claim 1 wherein R$_4$ is in the 9 position of the 1,4-benzodiazepine and is selected from the group consisting of nitro and trifluoromethyl.
4. The compound of claim 1 wherein R$_4$ is in the 10 position and is methoxy.
5. The compound of claim 1 wherein R$_4$ and R$_5$ together are selected from the group consisting of methylenedioxy and ethylenedioxy.
6. The compound of claim 1 wherein R$_1$, R$_2$, and R$_3$ are selected from the group consisting of trifluoromethyl, methylenedioxy, ethylenedioxy, F, Cl, Br, I, methyl and methoxy groups.

7. The 1,2,4,4a-tetrahydro-7-phenyl-5H[1,4]oxazino[4,3-a]-[1,4]benzodiazepine compound of claim 1 wherein $R_1$, $R_2$ and $R_3$ are hydrogen and $R_4$ is hydrogen and $R_5$ is selected from the group consisting of hydrogen 9-fluoro, 9-chloro, 10-methoxy, 9-bromo, 9-trifluoromethyl, 9-nitro, 11-nitro, 9-methyl, 10-methyl, or $R_4$ is 9-methyl and $R_5$ is 10-methyl, or $R_4$ is 9-chloro and $R_5$ is 10-chloro or $R_4$ is 10-chloro and $R_5$ is 9-methyl, or $R_4$ and $R_5$ together are 9,10-methylenedioxy, or $R_4$ is 9-bromo and $R_5$ is 10-methyl.

8. The 1,2,4,4a-tetrahydro-7-phenyl-5H[1,4]oxazino[4,3-a][1,4]benzodiazepine compound of claim 1 wherein $R_1$, $R_2$, $R_3$ and $R_4$, $R_5$ are selected from the following groups:
   (i) $R_4$ is hydrogen and $R_5$ is hydrogen, 9-chloro, 9-nitro or 11-nitro and $R_1$ is 2'-chloro and $R_2$ and $R_3$ are hydrogen
   (ii) $R_4$ is hydrogen and $R_5$ is hydrogen or 9-bromo and $R_1$ is 2'-fluoro and $R_2$ and $R_3$ are hydrogen
   (iii) $R_4$ is hydrogen and $R_5$ is 9-chloro and $R_1$ is 3'-trifluoromethyl and $R_2$ and $R_3$ are hydrogen or $R_1$ is 3'-chloro, $R_2$ is 4'-chloro, and $R_3$ is hydrogen and
   iii) $R_4$ is hydrogen and $R_5$ is 9-fluoro and $R_1$, $R_2$ and $R_3$ are 3'4',5'-trimethoxy.

9. The 1,2,4,4a-tetrahydro-7-phenyl-5H[1,4]thiazino[4,3-a][1,4]benzodiazepine compound of claim 1 wherein $R_4$ and $R_5$ and $R_1$, $R_2$, $R_3$ are selected from the following groups:
   (i) $R_4$ is hydrogen and $R_5$ is hydrogen, 9-chloro, 9-fluoro, 9-nitro, 9-methyl or 10-methoxy and $R_1$, $R_2$, $R_3$ and hydrogen
   (ii) $R_4$ is hydrogen, $R_5$ is 9-chloro and $R_1$ is 3'-trifluoromethyl and $R_2$ and $R_3$ are hydrogen, and
   (iii) $R_4$ and $R_5$ are hydrogen and $R_1$ is 2'-fluoro and $R_2$ and $R_3$ are hydrogen.

10. The 1,2,3,4,4a,5-hexahydro-7-phenyl-pyrazino[1,2-a][1,4]benzodiazepine compound of claim 1, wherein $R_1$, $R_2$, $R_3$, $R_4$ are hydrogen $R_5$ is 9-chloro and R is selected from the group consisting of hydrogen, methyl, isopropyl, butyl, tert.-butyl, isopentyl, neopentyl, allyl, β-hydroxyethyl, β-chloroethyl, β-methoxyethyl, 3-hydroxypropyl, benzyl, phenethyl and 3,4-dimethoxyphenethyl.

11. The 1,2,3,4,4a,5-hexahydro-7-phenyl-pyrazino[1,2-a][1,4]benzodiazepine compound of claim 1, wherein R is methyl and $R_4$, $R_5$ and $R_1$, $R_2$, $R_3$ are selected from the following groups:
   (i) $R_4$ is hydrogen, $R_5$ is hydrogen, 9-fluoro, 9-nitro, 10-methoxy, 9-methyl, 10-methyl, or $R_4$ is 9-methyl and $R_5$ is 10-methyl or $R_4$ is 9-chloro and $R_5$ is 10-chloro and $R_1$, $R_2$, $R_3$ are hydrogen
   (ii) $R_4$ is hydrogen $R_5$ is hydrogen, 9-chloro, 10-methyl, or $R_4$ is 9-bromo and $R_5$ is 10-methyl and $R_1$ is 2'-chloro and $R_2$ and $R_3$ are hydrogen and
   (iii) $R_4$ is hydrogen and $R_5$ is 9chloro and $R_1$ is 2'-methoxy and $R_2$ and $R_3$ are hydrogen.

12. The 1,2,3,4,4a,5-hexahydro-7-phenyl-pyrazino-[1,2-a][1,4]benzodiazepine compound of claim 1, wherein R is hydrogen and $R_4$, $R_5$ and $R_1$, $R_2$ and $R_3$ are selected from the following groups:
   (i) $R_4$ is hydrogen and $R_5$ is hydrogen, 10-methoxy, 9-bromo, 9-methyl, or $R_4$ is 9-methyl, $R_5$ is 10-methyl or $R_4$ is 9-bromo and $R_5$ is 10-methyl and $R_1$, $R_2$ and $R_3$ are hydrogen
   (ii) $R_4$ is hydrogen and $R_5$ is 9-chloro and $R_1$ is 2'-chloro and $R_2$ and $R_3$ are hydrogen or $R_1$ is 3'-chloro, $R_2$ is 4'-chloro and $R_3$ is hydrogen and
   (iii) $R_4$ is hydrogen, $R_5$ is 9-bromo and $R_1$ is 3'-chloro, $R_2$ is 4'-chloro and $R_3$ is hydrogen.

13. A pharmaceutical ulcer treatment composition comprising the compound defined in claim 1 and a pharmacologically inert carrier.

14. Compositions as defined in claim 13 in solid or liquid form adapted for oral use.

15. Compositions as claimed in claim 14 in tablet form.

16. Compositions as claimed in claim 15 adapted for administration by injection.

17. Compositions as claimed in claim 13 in dosage unit form with each dosage unit containing an effective amount of said compound.

18. Compositions according to claim 17 in dosage unit form in which dosage unit contains from about 5 to about 500 mg of said compound.

19. Compositions according to claim 18 in which each dosage unit contains from about 50 to 100 mg of said compound.

20. A method of treating a patient for relief of an ulcer condition comprising the step of administering to said patient an amount of the compound claimed in claim 1 effective to relieve said condition.

21. A pharmaceutical composition for the treatment of an ulcer condition in a patient comprising an ulcer treating amount of the compound defined in claim 1 and a pharmacologically inert carrier.

22. The compound of claim 1 comprising 1,2,4,4a-tetrahydro-9-chloro-7-phenyl-5H[1,4]oxazino-[4,3-a][1,4]benzodiazepine.

* * * * *